US006312897B1

(12) United States Patent
Verdine et al.

(10) Patent No.: US 6,312,897 B1

(45) Date of Patent: Nov. 6, 2001

(54) TEMPLATE-DIRECTED INTERFERENCE FOOTPRINTING OF PROTEIN-ADENINE CONTACTS

(75) Inventors: Gregory L. Verdine, Lexington, MA (US); Timothy D. Cushing, Pacifica, CA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/214,207

(22) PCT Filed: Jun. 30, 1997

(86) PCT No.: PCT/US97/11684

§ 371 Date: Nov. 4, 1999

§ 102(e) Date: Nov. 4, 1999

(87) PCT Pub. No.: WO98/00433

PCT Pub. Date: Jan. 8, 1998

Related U.S. Application Data

(60) Provisional application No. 60/021,238, filed on Jul. 3, 1996.

(51) Int. Cl.[7] .......... C12Q 1/68

(52) U.S. Cl. .......... 435/6; 536/24.3

(58) Field of Search .......... 435/6; 536/24.3

(56) References Cited

U.S. PATENT DOCUMENTS 5,512,131 4/1996 Kumar et al. .

FOREIGN PATENT DOCUMENTS 0 710 667 A2 A3 5/1996 (EP) .
WO9424144A 10/1994 (WO) .
WO96/29629 6/1996 (WO) .

OTHER PUBLICATIONS

C. Min et al., "Template–Directed Interference Footprinting of Protein–Adenine Contacts," *Journal of the American Chemistry Society*, vol. 118, No. 26, Jun. 1996, pp. 6116–6120.

J.L. Mascarenas et al., "Template–Directed Interference Footprinting of Protein–Thymine Contacts," *Journal of the American Chemical Society*, vol. 115, No. 1. Jan. 1993, pp. 373–374.

K.C. Hayashibara & G.L. Verdine, "Template–Directed Interference Footprinting of Cytosine Contacts in a Protein–DNA Complex: Potent Interference by 5–aza–2'deoxycytidine," *Biochemistry*, vol. 31, No. 46, 1992, Easton, PA US, pp. 11265–11273.

K.C. Hayashibara & G.L. Verdine, "Template–Directed Interference Footprinting of Protein–Guanine Contacts in DNA," *Journal of the American Chemical Society*, vol. 113, No. 13, 1991, DC US, pp. 5104–5106.

K.F. Lau & J.F. Henderson, "Inhibitors of Purine Metabolism in Ehrlich Ascites Tumor Cells in Vitro," *Cancer Chemother. Rep. Part. 2*, vol. 3, No. 1, 1972, pp. 95–109.

Sidney M. Hecht, "Bioorganic Chemistry: Nucleic Acids," *Oxford University Press*, 1996.

Min, C., Verdine, G., "Immobilized Metal Affinity Chromatography of DNA," *Nucleic Acids Res.* 1996, 24, 3806–3810.

*Primary Examiner*—Scott W. Houtteman

(74) *Attorney, Agent, or Firm*—Wolf, Greenfield & Sacks, P.C.

(57) ABSTRACT

A chemical analog of adenine is provided which can be incorporated into DNA but base pairs as normal, and does not disrupt DNA secondary structure. The analog is cleavable and disrupts functionality with DNA-binding protein. The analog finds use in a technique provided by the invention involving TDI footprinting or adenine-DNA contacts.

24 Claims, 1 Drawing Sheet

TEMPLATE-DIRECTED INTERFERENCE FOOTPRINTING OF PROTEIN-ADENINE CONTACTS

This application is a 371 of PCT/US97/11684 filed Jun. 30, 1997, and also claims the benefit of U.S. Provisional No. 60/021,238 filed Jul. 3, 1996.

This invention was supported by NSF Grant Number MCB-9158086. The government has certain rights to the invention.

FIELD OF THE INVENTION

The present invention relates generally to the study of protein-DNA interactions, and more particularly to a technique for inhibiting protein-adenine noncovalent contacts without disrupting the secondary structure of DNA, thereby providing a template-directed interference technique for precisely studying protein-DNA interactions.

BACKGROUND OF THE INVENTION

The study of molecular recognition at the interface between protein and DNA is of paramount importance in the study of protein regulation of gene expression. Such protein-DNA recognition involves noncovalent interaction (hydrogen bonding, ionic interactions, and nonpolar interactions) between nitrogen bases of DNA and amino acids of protein characterized by great stability and specificity.

A variety of techniques, referred to as DNA footprinting, have been developed to study these interactions. These techniques typically involve chemical alteration of DNA to inhibit interaction with protein, exposure of the DNA to protein, separation of protein-bound DNA from unbound DNA, and subsequent DNA cleavage and sequencing, or exposure of DNA to protein followed by addition of a chemical moiety that will interact with DNA except where protected by protein, followed by cleavage and sequencing. The results of a polyacrylamide sequencing gel can identify the location of protein binding in these procedures via identification of a lack of DNA fragments in a molecular weight region that would have been present without protein binding at a specific location, or presence of bands signifying DNA fragments that are present because DNA was not allowed to bind at a specific location.

Specifically, in "DNA protection footprinting", protein is bound to end-labeled DNA and the resulting complex is treated with a reagent that interacts with DNA (but not at regions bound to protein) to produce chemical lesions that give rise to strand cleavage. The conditions of treatment are adjusted such that each DNA molecule receives statistically one lesion, thereby producing a statistical mixture of singly-modified DNA molecules each including a cleavage site at a random position along the DNA chain, but not at the site of protein binding. Subsequent cleavage and gel sequencing of the cleaved, protein-bound DNA, and comparison with a sequenced control of DNA treated identically but without protein binding, results in a lack of bands associated with protein binding positions.

"DNA interference footprinting" involves treatment of end-labeled DNA with a reagent that prevents protein binding and provides a cleavage site, to produce a probe of statistically singly-modified DNA molecules. The pool of DNA is incubated with DNA-binding protein, protein-bound DNA is separated from unbound DNA, and both populations are subjected to cleavage conditions. The resulting fragments are separated on a sequencing gel and, by comparison of the bands representing bound DNA with bands representing unbound DNA, a lack of bands in the protein-bound fraction and presence of bands in the protein-unbound fraction, each in a region corresponding to a molecular weight distribution of fragmentation at a particular location on the DNA, is indicative of protein binding at that region.

Other footprinting techniques, such as DNase I footprinting, Exonuclease III footprinting, hydroxyl radical footprinting, diethyl pyrocarbonate footprinting, $KMnO_4$ and $OsO_4$ footprinting, ethylation interference footprinting, uranyl photofootprinting, methylation protection and methylation interference footprinting, and missing contact footprinting are known and are described by C. J. Larson and G. L. Verdine, "The Chemistry of Protein-DNA Interactions", *Bioorganic Chemistry: Nucleic Acids*, S. M. Hecht, Ed., Oxford University Press, New York, 1996, pages 324–342. Most of the above techniques do not provide information as to which groove of DNA, major or minor, is involved in binding.

An optimal footprinting method for determining specific base contacts at Protein-DNA binding sites should possess a number of characteristics, including the following: (1) the method should be capable of assaying contacts to all four bases in both the major groove and the minor groove of DNA, (2) the structure of the interfering probe moiety should be known, (3) the interference probe should minimally perturb DNA secondary structure relative to its natural counterpart, and (4) the method should be operationally simple. Unfortunately, many of the footprinting methods described above fall short of these goals since they involve attachment of a chemical moiety to DNA that can affect larger-scale phenomena such as DNA conformation.

Accordingly, template-directed interference (TDI) footprinting (described also in the above-reference article of Larson and Verdine) has been developed to circumvent the chemical reagent-based approach. TDI footprinting relies upon the ability to incorporate, in the DNA polymer itself, a molecule that is similar enough to one of the nucleic acids to avoid disruption of DNA secondary structure, that possesses the ability to base-pair as would a normal nucleotide, but that disrupts protein-DNA interaction, and is cleavable. TDI footprinting offers significant advantage over others of the above-described footprinting methods in that alteration of DNA secondary structure is avoided, and DNA and/or protein is not induced to act in a manner inconsistent with natural protein/DNA bonding.

Although TDI footprinting offers significant advantage in the study of protein-DNA interaction, availability of the necessary nitrogen base analogs for the technique is limited because of the challenging requirements discussed above. TDI footprinting analogs of guanine, cytosine, and thymine have been reported (Hayashibara, K. C., Verdine, G. L., *J. Am. Chem, Soc.,* 1991, 113, 5104–5106; Hayashibara, K. C., Verdine, G. L., *Biochemistry,* 1992, 31, 11265–11273; Mascareñas, J. L., Hayashibara, K. C., Verdine, G. L., *J. Am. Chem. Soc.,* 1993, 115, 373–374, respectively). However, although TDI footprinting has been known since at least 1991, and cited extensively, TDI footprinting of the DNA base adenine has remained elusive. Significantly, without an available, suitable TDI footprinting analog of adenine, TDI footprinting as a technique has been constrained in that it could not be used to analyze contacts to the base surface of the entire major groove of DNA, the principal locus of sequence-specific interactions in protein-DNA complexes.

It is, therefore, an object of the present invention to provide TDI footprinting involving adenine.

SUMMARY OF THE INVENTION

The present invention provides a molecule that mimics adenine, in that it can be incorporated into DNA without adversely affecting normal base pairing to thymine, but that disrupts adenine-dependant DNA binding to proteins. The molecule find particular utility in a method also provided by the invention that involves study of protein-DNA interaction.

The molecule of the invention has a formula:

(I)

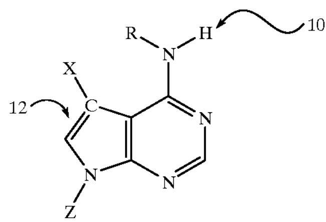

where X is a moiety allowing cleavage of double bond 12 under conditions tolerable by a protein-DNA complex, R is H or a hydrocarbon, and Z is an oligonucleotide, 2'-deoxyribose-5-'triphosphate, or a functionality attachable to an oligonucleotide (which can be selected by one of ordinary skill in the art). According to another aspect of the invention, an oligonucleotide, such as DNA, including at least one nitrogen base of the above formula is provided.

A method of the invention involves a technique for determining contacts in a protein-DNA complex. A plurality of end-labeled DNA strands are provided, each including, statistically, a nitrogen base of the above formula. A DNA-binding protein is added to the plurality of strands, protein-bound DNA is separated from unbound DNA, and the DNA strands are cleaved. The strands then are sequenced to determine a molecular weight region populated predominantly by the unbound strands, representative of cleavage sites indicating a protein-binding site.

The invention also provides a method of determining contacts in a protein-DNA complex, involving investigation with TDI footprinting analogs of all four DNA bases. The technique involves providing four groups of DNA. The first three groups include, respectively, a plurality of end-labeled DNA strands that each have, statistically, a TDI footprinting base analog of guanine, cytosine, or thymine. The fourth group includes a plurality of end-labeled DNA strands that each have, statistically, a TDI footprinting base analog of adenine having a formula I, above. A DNA-binding protein is added to each group, protein-bound DNA is separated from unbound DNA, the DNA strands are cleaved, and the strands are sequenced to determine a molecular weight region populated predominantly by the unbound strands and representative of cleavage sites indicating a protein binding site. Provision of, and use in TDI footprinting of, TDI footprinting base analogs of guanine, cytosine, and thymine is described in the above-noted articles of Hayashibara, K. C., Verdine, G. L., *J. Am. Chem. Soc.,* 1991, 113, 5104–5106; Hayashibara, K. C., Verdine, G. L., *Biochemistry,* 1992, 31, 11265–11273; Mascareñas, J. L., Hayashibara, K. C., Verdine, G. L., *J. Am. Chem. Soc.,* 1993, 115, 373–374, respectively, all incorporated herein by reference.

Other advantages, novel features, and objects of the invention will become apparent from the following detailed description of the invention when considered in conjunction with the accompanying drawing.

DETAILED DESCRIPTION OF THE INVENTION

Figure 1:
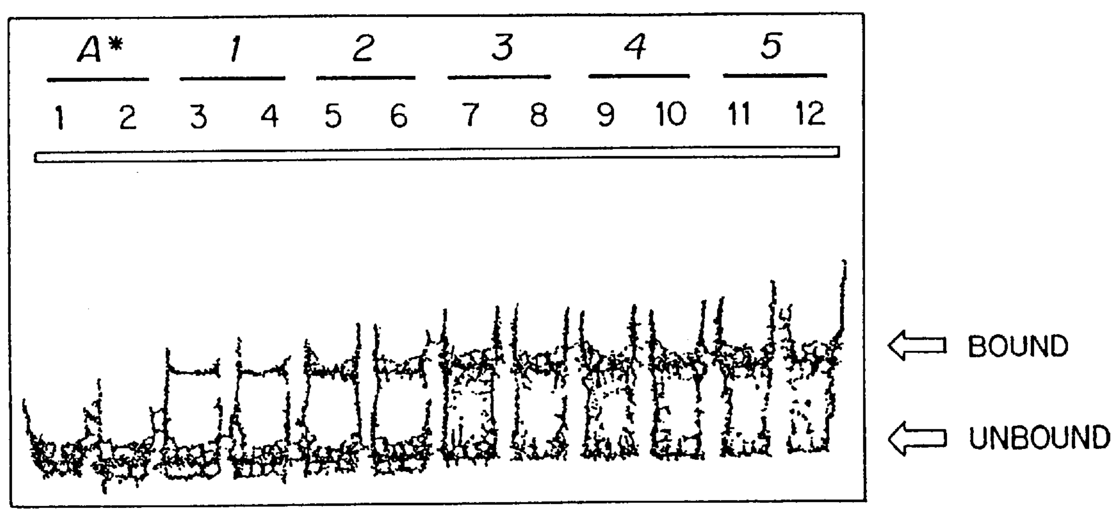
FIG. 1 is a photocopy of nondenaturing polyacrylamide gel electrophoresis (PAGE) of mixtures containing a pool of the inventive adenine analog—substituted DNA and various concentrations of protein.

Min, C., Cushing, T. Verdine, G., "Template-Directed Interference Footprinting of Protein-Adenine Contacts,", *J. Am. Chem. Soc.* 1996, 118, 6116–6120; and Min, C. Verdine, G., "Immobilized Metal Affinity Chromatography of DNA," *Nucleic Acids Res.* 1996, 24, 3806–3810, both are incorporated herein by reference.

The role of hydrogen bonding in protein-DNA interactions is very important, as hydrogen bonds normally make up a large fraction of the total number of contacts in a protein-DNA complex. Although it is generally accepted that hydrogen bonds contribute only modestly to the overall energetics of specific complexation, they serve a critical role in determining the specificity of protein-DNA interactions. Formation of matched sets of bonds including hydrogen bonds to DNA bases of the optimal binding site allows the entire protein to come into intimate contact with the DNA surface, permitting the formation of a large number of energetically favorable nonspecific contacts.

The present invention provides an analog of the DNA base adenine, having the generalized formula I, as described above. When R is selected as H, either X is selected so as not to be amenable to hydrogen bonding (so as not to hydrogen-bond with an adjacent species) or X is selected so as to hydrogen bond with R so as to prevent hydrogen bonding between R and an adjacent species. When X is selected so as not to be amenable to hydrogen bonding, it is, for example, selected from moieties other than F, N, and O. When R is selected as a group not including a H amenable to hydrogen bonding, X can be a moiety amenable to hydrogen bonding.

R and X should be selected, together, so as not to alter the conformation of species I in a manner that would prevent species I from participating in normal Watson-Crick bonding. That is, they should be selected so as not to sterically interact in a way that would cause species I to twist appreciably.

Preferably, R is H or a hydrocarbon group (including cyclic hydrocarbon groups), optionally interrupted by hetero groups. As used herein, "hydrocarbon" is meant to include alkyl, alkenyl, alkynyl, cycloalkyl, aryl, alkaryl, aralkyl, and the like. Hetero groups can include —O—, —CONH—, —CONHCO—, —NH—, —CSNH—, —CO—, —CS—, —S—, —SO—, —$(OCH_2CH_2)_n$R (where n=1–10), —$(CF_2)_n$— (where n=1–10), olefins, and the like. Most preferably, R is a small moiety such as H or $CH_3$. R should be selected so as not to interfere with hydrogen bonding between H 10 and thymine.

X is a moiety allowing cleavage of double bond 12 under conditions tolerable by a protein-DNA complex. Those of ordinary skill in the art can routinely select X according to this criterion. Typically, X has electron-withdrawing capacity sufficient to render double bond 12 readily cleavable by, for example, aqueous base, so that the TDI footprinting technique described above, and described in the above-referenced article of Larson and Verdine can be carried out. In this case X is, preferably, an electron-withdrawing group such as —CN, —Br, —Cl, —$NO_2$, —$SO_3^-$, —$SO_2$R, —COOH, —F, or the like. Alternatively, X can be an electron-donating group including electron-donating capacity sufficient such that bond 12 can be cleaved by permanganate, followed by base. In this case, X can be $—OCH_3$, $—CH_3$, —OH, —Ar (aromatic), $—NHCOCH_3$, or the like.

R and X can, together, define a connected, or cyclic, moiety, as will be appreciated by those of skill in the art.

According to one, particularly preferred embodiment where R is H, X is $—NO_2$ and interacts by hydrogen bonding with R, preventing hydrogen bonding between R and protein.

The molecule I of the invention satisfies the following criteria. First, as part of an oligonucleotide, such as DNA, it does not disrupt secondary structure of the oligonucleotide. Second, it is cleavable chemically at double bond 12 so as to find utility in TDI footprinting. Third, it disrupts functionality with protein, achievable when the selection of X and R is made according to the criteria above. Finally, it is amenable to normal base pairing with thymine, that is, atoms involved in Watson-Crick hydrogen bonding are not be altered.

Referring now to structure II, Watson-Crick hydrogen bonding between adenine 14 and thymine 15 in DNA is illustrated. Adenine 14

(II)

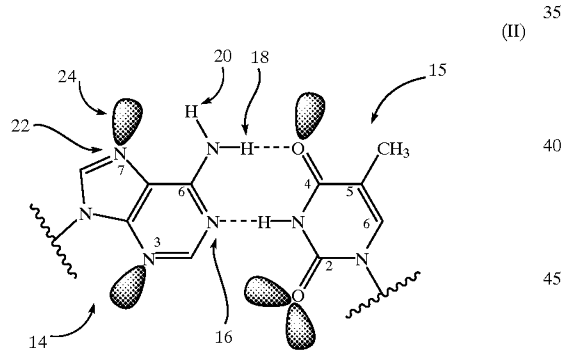

includes nitrogen 16 and hydrogen 18, involved in hydrogen bonding with thymine, which hydrogen bonding is not disrupted in accordance with the invention. Natural adenine includes as well hydrogen 20 and nitrogen 22 (including representative electron cloud 24), both of which are amenable to hydrogen bonding with protein interacting with DNA, at least one of which is prevented front hydrogen bonding in accordance with the invention.

Referring now to arrangement III, adenine 14 and thymine 15 are shown as paired in DNA, and a portion 26 of the protein glutamine is illustrated including hydrogen 28 which is hydrogen-bonded to nitrogen 22 of adenine, and oxygen 30, hydrogen-bonded to hydrogen 20 of adenine (see Larson and Verdine, "The Chemistry of Protein-DNA Interactions" referenced above, page 329).

(III)

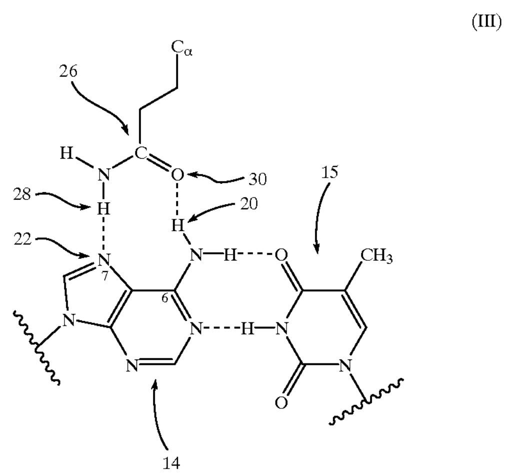

It is one of these hydrogen bonds, between hydrogen 28 and nitrogen 22, or between oxygen 30 and hydrogen 20, that is to be disrupted in accordance with the invention. Preferably, both are disrupted.

According to one preferred embodiment of the invention (with reference to formula I), X is $—NO_2$, and R is H. This molecule, illustrated as formula IV below, allows for hydrogen bonding between X and R, namely between oxygen 32 and hydrogen 34 (R), precluding any hydrogen bonding between X or R and a protein.

(IV)

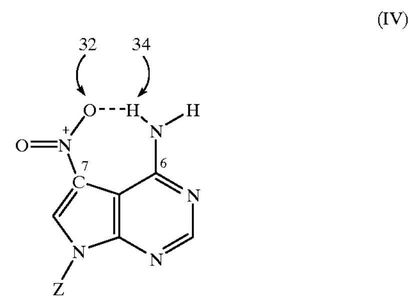

The function and advantage of these and other embodiments of the present invention will be more fully understood from the examples below. The following examples are intended to illustrate the benefits of the present invention, but do not exemplify the full scope of the invention. References cited in the following example is incorporated herein by reference for all purposes.

Example 1

Synthesis of Analog Suitable for TDI Footprinting of Major Groove Contacts to Adenine This and the following examples are directed toward the synthesis and validation of an adenine analog suitable for TDI footprinting. A species having the generalized formula (I), specifically 7-deaza-7-nitroadenine.

Materials: 7-Deaza-2'-deoxyadenosine (2'-deoxytubercidin) (Cottam, H. B.; Kazimicrrczuk, Z.; Geary, S.; McKernan, P. A.; Revankar, G. R.; Robins. R. L., *J. Med. Chem.* 1985, 28 1452–1467) was obtained from Boehringer Mannheim. Naturally occurring dNTPs were from Pharmacia (Piscataway, N.J.). Taq polymerase was from Promega (Milwaukee, Wis.). T4 polynucleotide kinase was from Gibco BRL (Gaithersburg, Md.), and glycogen was from Boehringer Mannheim (Indianapolis, Ind.). Sequenase 2.0 and the Sequenase 2.0 kit were from United States Biochemical (Cleveland, Ohio). [$\gamma$-$^{32}$P] ATP was from New England Nuclear. Full-length 434 repressor was expressed in *Escherichia coli* using XA90/pRW190 and purified as described (Anderson, J.; Ptashne, M.; Harrison, S. C. *Proc. Natl. Acad. Sci. U.S.A.* 1984, 81, 1307–1311).

Synthesis of 4-Amino-7-(2-deoxy-3,5-diacetoxy-β-D-erythro-pentofuranosyl)pyrrolo[2,3-d]pyridimine (2): To a stirred suspension of 4-amino-7-(2-deoxy-β-D-erythro-pentofuranosyl)poyrrolo[2,3-d]pyrimidine (2'-deoxytubercidin, 1) (Cottam et al., above) in pyridine (1.6 mL, 0.4 M) at 0° C. under $N_2$ was added acetic anhydride (0.33 mL, 3.5 mmol. 5.3 equiv). The mixture was allowed to stir overnight, reaching ambient temperature in that time. The solution was diluted with methanol (3 mL), stirred briefly, reduced to dryness, and was placed on the vacuum line for a few moments. The residue was then subjected to a refluxing solution of methanol (3 mL) for 12 h. The solution was again reduced to dryness, yielding 240 mg of a crude solid. Chromatography: flash column (20 g of silica) 2% MeOH/$CH_2Cl_2$ to 5% MeOH/$CH_2Cl_2$. The product was obtained as a white foamy solid. Yield: 187 mg, 85% $^1$H NMR (300 MHZ) ($CDCl_3$ relative to TMS) δ2.09 (6H, s); 2.48 (1H, ddd, J-2.1, 4.7, 14.0 Hz); 2.59–2.69 (1H, m); 4.27–4.37 (3H, m); 5.31–5.34 (1H, m); 5.61 (2H, br) exchanged); 6.41 (1H, d, J=1.0, 3.7 Hz); 6.68 (1H, dd, J=5.7, 8.7 Hz); 7.11 (1H, 3, J=3.7 Hz); 8.29 (1H, s). $^{13}$C NMR (126 MHZ) ($CDCl_3$): δ20.76, 20.87, 37.44, 64.02, 74.63, 81.54, 83.49, 99.44, 103.89, 120.89, 140.67, 151.98, 156.88, 170.38. IR (thin film, $CDCl_3$): 3152, 1740, 1734, 1684, 1653, 1233 cm$^{-1}$. MS (El): m/e (rel intens) 334 ($M^+$, 0.1); 275 (0.5); 134 (100); 107 (0.15). El HRMS ($Cl^+$)(M+1): 335.1355 ($C_{15}H_{18}N_4O_5$ requires 334.3328).

Synthesis of 4-Amino-5-nitro-7-(2-deoxy-3,5-diacetoxy-β-D-erythro-pentofuranosyl)pyrrolo[2,3-d]pyridimine (3): To a vigorously stirred 0° C. solution of 2 (97.9 mg, 0.29 mmol, 1.0 equiv) in $CH_2Cl_2$ (1.9 mL, 0.15 M) was added a mixture of concentrated $H_2SO_4$ (320 mg) and fuming $HNO_3$ (260 mg) in a dropwise fashion. After 20 min the ice bath was removed and the biphasic solution stirred for an additional 20 min and then neutralized with a saturated $NaHCO_3$ solution until the pH reached 7.0. The mixture was extracted with $CH_2Cl_2$ (~200 mL), and the bright yellow solution was washed with brine, dried over $MgSO_4$, and reduced to dryness. Crude yield: 6.33 mg, 60%. The resulting dark yellow solid was used without further purification. $^1$H NMR ($300_{MHZ}$) ($CDCl_3$): δ2.09 (3H, s); 2.14 (3H, s); 2.49–2.58 (1H, m); 2.68 (11H, ddd, J=3.1, 6.0, 17.2 Hz); 4.34 (3H, br s): 5.31 (1H, m); 6.40 (1H, br s, $D_2O$ exchanged); 6.62 (1H, t, J-6.4 Hz); 7.56 (1H hrs $D_2O$ exchanged); 8.26 (1H, s); 8.276 (1H, s). $^{13}$C NMR (126 MHZ) ($CDCl_3$): δ20.69, 20.79, 38.82, 63.53, 73.83, 82.62, 84.62, 95.74, 95.78, 125.15, 129.55, 149.56, 154.12, 156.41, 170.23, 170.30 IR (thin film, $CDCl_3$): 3150, 1740, 1734, 1684, 1653, 1570, 1522, 1506, 1234 cm$^{-1}$. MS (Cl): m/e (rel intens) 380 (M=1, 0.2); 294 (0.60); 236 (100).

Synthesis of 4-Amino-5-nitro-7-(2-deoxy-β-D-erythro-pentofuranosyl)pyrrolo[2,3-d]pyridimine (4): To a stirred solution of 3 (17.4 mg,, 0.046 mmol, 1.0 equiv) under $N_2$ at 0° C. in methanol (1.3 mL) was added $H_2CO_3$ (13 mg, 0.10 mmol, 2.2 equiv. After 20 min the reaction mixture was diluted with brine (25 mL) and extracted with ethyl acetate (100 mL). The aqueous layer was then re-extracted with ethyl acetate (3×50 mL), and the organic fractions were combined, dried over $MgSO_4$, and evaporated to yield a bright yellow solid. Chromatography: PTLC 5% MeOH/$CH_2$—$Cl_2$. Yield: 8.8 mg, 65% $^1$H NMR (300 MHZ) (methanol-$d_4$): δ2.42–2.48 (1H, m); 2.53–260 (1H, m); 3.73–3.87 (2H, m); 4.03 (1H, t, J=2.9 Hz); 4.53 (111, dd, J=1 8, 2.9 Hz); 4.86 (2H, s, $D_2O$ exchanged); 4.87 (2H, s,$D_2O$ exchanged); 6.57 (1H, dd, J=4.4, 6.2 Hz); 8.17 (1H, d, J=2.5 Hz); 8.70 (1H, d, J=2.5 Hz). $^{13}$C NMR (126 MHz) (methanol-$d_4$): δ41.73, 62.75, 72.14, 86.87, 89.22, 96.88, 128.70, 130.12, 150.12, 154.75, 157.96. IR (thin film, MeOH): 3445–3335 br, 1684, 1653, 1570, 1522, 1507, 1269 cm$^{-1}$. MS (El): m/e (rel intens) 295 ($M^+$, 0.1); 200 (0.25); 179 (100). El HRMS: m/e 295.0904 ($C_{11}H_{13}N_5O_5$ requires 295.0917). Mp: 186–190° C.

Synthesis of 7-deaza-7-nitro-2'-deoxyadenosine 5'-Triphosphate (dA*TP,5): To a stirred solution of 4 (4.1 mg, 14 μmol, 1.0 equiv) at 0° C. under $N_2$ in dry trimethyl phosphate (50 μL) was added $POCl_3$ (1.7μL, 18 μmol), 1.3 equiv). After 15 h a solution of tris-(tributylammonium) pyrophosphate (0.14 mL, 1 M, in DMF) was added to the reaction flask, and stirred overnight (0° C. to room temperature). At this time $Et_3N$ (43 μL) and $H_2O$-$d_2$ (612 μL) were added to the flask and stirred for 5 min. The mixture was lyophilized and the residue dissolved in 100 μL of $H_2O$-$d_2$ and passed through an ion exchange column (Sephadex A25, 1 g) equilibrated in 0.1 M aqueous triethylammonium bicarbonate (TEAB). The column was washed with 50 mL of $H_2O$-$d_2$ and then eluted with 950 mL gradient from 0 to 2 M triethylammonium bicarbonate, with 10 mL fractions being collected. Fractions 11–27 were combined and lyophilized to dryness, and the remaining white powder was redissolved in 1 mL of TE buffer: 10 mM Tris-HCl (pH 8.0), 1 mM EDTA. This solution was used directly in extension reactions with Sequenases 2.0. The yield was estimated to be 5.7 μmol (41%) by spectrophotometric analysis using the reported extinction coefficient ($\lambda_{max}$=365 nm, ε=3900) for the related compound 5-nitrotubercidin[9]. $^{34}$P NMR (202 MHz) ($D_2O$ referenced to phosphoric acid): δ-5.4(d); -6.1 (m); -19.5 (m). UV($H_2O$): $\lambda_{max}$=356, 364 nm.

Example 2

Confirmation of the Ability of the Species of Example 1 to Promote Ring Fragmentation and DNA Strand Scission 7-deaza-7-nitro-2'-deoxyadenine (dA*) was synthesized by nitration of 2'-deoxytubercidin. A sample of dA* was dissolved in 1 M aqueous piperidine at 90° C., and aliquots were periodically removed and spotted onto a TLC plate. Analysis of the resulting TLC plate revealed virtually complete disappearance of the dA* chromophore within 30 min. These data indicated that the base moiety of dA* undergoes hydrolytic degradation under the conditions used in piperdine-catalyzed cleavage of DNA, thus it is possible to cleave DNA selectively at positions containing the analog.

Example 3

Incorporation of 7-deaza-7-nitroadenine (dA*) into DNA

Preparation of Single-Stranded Template DNA by PCR/IMAC (PCR/metal affinity chromatography): Complementary oligonucleotides containing the operator and flanking sequences used in the crystallographic study of the 434 repressor (N-terminal domain)/$O_R1$ complex were synthesized with 3'-PstI-compatible ends, ligated into the PstI site in the polylinker of the phagemid pBS+ (Stratagene), and transformed into *E. coli* strain XL1-blue (Stratagene). Insert-positive recominants (designated pBS-434) were verified by sequencing of single-stranded phagemid DNA isolated from helper phage VCS-M13 (Stratagene). Hayashibara, K. C. PhD. Thesis, Harvard University, Cambridge, Mass. 1993.

The polymerase chain reaction followed by immobilized metal affinity chromatography (PCR/IMAC) was used to generate single-stranded DNA templates containing the operator sequence. This technique is reported in a co-pending, commonly-owned United States provisional patent application of Verdine, et al., filed Jul. 3, 1996 (Ser. No. 60/021,195) and in Min, C, Verdine, G., "Immobilized Metal Affinity Chromatography of DNA," *Nucleic Acids Res.* 1996, 24, 3806–3810, both incorporated herein by reference. In the technique, a moiety that can coordinate a metal ion is inserted into DNA. Specifically, DNA sequencing primers containing six successive 6-histaminylpurine residues added onto the 5'-end of the DNA was synthesized. The PCR/IMAC technique is preferred, although other techniques can be used, such as an asymmetric PCR technique. Alternate techniques are discussed in the Min, et al., paper, *Nucleic Acids Res.,* 1996, 24, 3806, referenced above.

The 6-histaminylpurine moiety was introduced through the convertible nucleotide approach by analogy to reported procedures (Ferentz, A. E.; Verdine, G. L., *J Am. Chem. Soc.* 1991, 113, 4000–4002; Ferentz, A. E.; Verdine, G. L. In *Nucleic Acids and Molecular Biology*; Eckstein, F., Lilley, D. M. J. Eds.; Springer-Verlag: Berlin, 1994; Vol. 8, pp. 14–40. Briefly, resin-bound oligonucleotides containing $O^6$-phenyl-2'-deoxyinosine (Φd1) in place of the dH residue were deprotected from the resin by mild ammonia treatment (conc $NH_4OH$, nt, 4b) lyophilized to dryness, then treated with 5 M aqueous histamine (55° C., 14 h) to convert the Φd1 residues to dH. The crude oligonucleotides were purified by denaturing polyacrylamide gel electrophoresis. An additional dG residue was added at the 5'-end to ensure efficient end-labeling using polynucleotide kinase.

The $H_6$-tag confers, upon an oligonucleotide, the ability to be selectively and reversibly retained on a surface, specifically $Ni^{2+}$-NTA-agarose. The result is a single strand of DNA immobilized at a surface.

Following removal of the supernatant, which contains unbound DNA, the resin was washed and the bound DNA eluted with 200 mM imidazole.

Amplification was carried out in a 100 μL PCR reaction mixture containing 50 mM KCl, 10 mM Tris-HCl (pH 8.4), 1.5 mM $MgCl_2$, 0.25 mM (each) dATP, dCTP, dGTP, and TTP, 1 unit of Taq polymerase, 20 μg of pBS434 as template, 50 pmol of $H_6$-tagged M13 (−48) primer [5'-d(GHHHHHHAGCGGATAACAATTTCACACAGG)-3'], H=6-histaminylpurine, and 50 pmol of M13 (−47) primer [5'-dCGCCAGOGTTTTCCCAGTCACGA)-3']. The reaction solution was overlaid with a 60 μL mineral oil cap to prevent evaporation and placed in a thermal cycler (MJ Research) programmed for 35 cycles set at 94° C. (1 min), 55° C. (1 min) and 72° C. (1 min).

The duplex PCR products were resolved by IMAC as follows: 1 mL of TE buffer was added to the crude reaction mixture, which was then concentrated to a total volume of 50 μL using a centrifugal dialysis cartride (Centricon 30, Amicon). The DNA solution was transferred to an Eppendorf tube, to which was added 150 μL of binding buffer (6 M guanidine-HCl, 10 mM Tris, pH 8.2). This mixture was heated for 5 min at 90° C. Separately, to a 1.5 mL Eppendorf tube was added 250 μL (bed volume) of $Ni^{2+}$-NTA agarose resin and 1 mL of binding buffer at room temperature. The hot DNA solution was added to the suspension of resin, and the resulting mixture was mixed for 1–1.5 min by vigorous shaking. The mixture was transferred to an empty 5 mL fitted column (Qiagen), and the flow-through fraction, which contained the unmodified strand, was collected into an Eppendorf tube. After repeated pipetting to ensure complete mixing, the unbound fractions were aliquotted into four Eppendorf tubes (300 μL each) and held aside for further processing. Next, the resin was washed with 1 mL of washing buffer (10 mM Tris, 5 mM imidazole, pH 8.0), which was discarded. The $H_6$-containing strand was then eluted in 1.2 mL of 200 mM aqueous imidazole solution. The imidazole eluate was mixed thoroughly and aliquotted into four Eppendorf tubes (300 μL each), to each of which were added 30 μL of 100 mM ethanolic 1,10-phenanthroline and 30 μL of 3 M aqueous NaOAc. To each of the unbound and bound fractions was added 900 μL of absolute ethanol (stored at −20° C.), and then the tubes were vortexed briefly and chilled for 30 min of powdered solid $CO_2$. The tubes were microcentrigued for 30 min at 15000 g. The supernatant was removed and the pellet washed with 200 μL of 80% aqueous EtOH (−20° C.). Following removal of the ethanol solution, the tubes were evaporated to dryness by centrifugal lyophilization (SpeedVac, Savant). To each dry tube was added 50 μL of TE buffer, and the DNA concentration was quantified by UV spectrophotometry. This procedure typically yields 5–10 pmol of the $H_6$-tagged template and the unmodified template (the primers are used in ~5–10 fold excess in the PCR reaction).

Template-Directed Extension: The procedure provides a sufficient template for 20 lanes on a DNA sequencing gel.

(a) End Labeling of Primer: A 20 μL volume of 0.2 pmol/μL M13 (−21) primer, 5'-d(GTAAAACGACGGCCAGT)-3', was end labeled in a 100 μL volume by adding 10 μL of 400 mM Tris-HCl (pH 7), 200 mM $MgCl_2$, 20 units of T4 polynucleotide kinase, and 4 μL of 6000 Ci/mmol [y-$^{32}$P]ATP. This mixture was incubated at 37° C. for 30 min, heated at 90° C. for 3 min, chilled on ice, and briefly microcentrifuged at 14000 rpm.

(b) Annealing: A 100 μL volume of the DNA template strand (approximately 0.04 pmol/μL in TE) was added to the end-labeled primer (100 μL) and heated to 65° C. for 5 min, and then allowed to reach room temperature while remaining in the bath. The condensate was recombined with the annealed primer/template solution by brief microcentrifugation.

(c) Primer Extension: A 200 sample μL of annealed primer/template (4 pmol) was combined with 70 μL of polymerization buffer [48 mM Tris-HCl (pH 7), 25 mM $MgCl_2$, 200 mM NaCl, 9 mM DTT, and 400 μg/μL BSA). The resulting solution was added to 200 μL of a mixture containing 80 μM each of dCTP, dGTP, and dTTP; and 80 μM (total nucleotide) 1:3 mixture of dA*TP and dATP; and 50 μM NaCL. The extension was allowed to proceed at 37° C. for 20 min and then stopped by addition of 200 μL of 3 M sodium acciate (pH 7.0), and precipitated at −70 ° C. with 20 μL of 20 mg/mL glycogen and 1800 μL of 100% ethanol. The pellet obtained after microcentrifugation at 14000 rpm for 30 min at 4° C. was washed with 80% aqueous ethanol and dried by lyophilization. The resulting DNA was dissolved in 80 μL of TE, 4 μL of which was then used for each subsequent incubation with protein.

Example 4

Binding Studies Involving Adenine Analog of the Invention Incorporated into DNA 1 mM $CaCl_2$, 100 μg/mL BSA, and 10% (v/v) glycerol: Protein-bound and unbound DNA were separated using a 5% low-ionic-strength nondenaturing polyacrylamide gel. (Chodish, L. A. *In Current Protocols in Molecular Biology;* Ausabel, F. M., Brent, R. Kingston, R. E., Moore, D. D., Smith, J. A. Seidman, J. G., Struhl, K., Eds; John Wiley and sons: New York, 1989; Vol. 2, pp 12.2.1–12.2.10). (37:1 monomer;methylenebisacryl-amide). The gel was exposed to BioMAX film (Kodak) for 5 h. Bands were visualized by autoradiography and excised from the gel using a razor blade. The gel slices were electroeluted into 130 μL of 10 M ammonium acetate using a V-channel apparatus (Harvard BioLabs) with 0.5× TBE [45 mM Tris-borate (pH 8.0), 0.5 mM EDTA] as running buffer. The DNA samples in 10 M ammonium acetate were precipitated directly by the addition of 3 volumes of 100% ethanol followed by precipitation as described above.

Cleavage and Sequencing Procedure. Each $^{32}P$-labeled dsDNA sample was redissolved in 50 μL of 1 M aqueous piperidine. This solution was heated at 90° C. for 30 min, cooled to room temperature, and microcentrifuged briefly. Samples were lyophilized, twice resuspended in 30 μL of $H_2O$-$d_2$ and lyophilized and then redissolved in 3 μL of TE and 2 μL of loading dye containing 95% formamine, 10 mM EDTA, 0.025% bromophenol blue, and 0.025% xylene cyanol. Samples were heated at 90° C. for 2 min and then loaded immediately onto a 7% polyacrylamide sequencing gel. The gel was visualized by autoradiography. The generation of an authentic sequence by Sanger sequencing made use of the Sequenase 2.0 kit (United States Biochemicals) according to the manufacturer's protocol. A volume of 2.5 μL of annealed [$^{32}$Pjprimer;template mixture was used in each dideoxy termination reaction.

High resolution electrophoretic analysis of the products arising from extension and cleavage resulted in a pattern of bands of the A* lanes matching precisely that in the Sanger dideoxy-A sequencing lane, thus indicating that the analog shows the same base-pairing preference as its natural counterpart.

The titration series was fractionated by nondenaturing polyacrylamide gel electrophresis (PAGE), which separates naked DNA from protein-bound DNA on the basis of differences in size (FIG. 1). The bound and unbound DNA Bands were extracted from the native PAGE gel, cleaved with piperidine, and analyzed on a high-resolution denaturing polyacrylamide gel. Interference was evident in a TDI-A footprint as positions in the sequence at which a band was weak or absent from the bound lanes and enriched in the unbound lanes, relative to the A* control. Such behavior was clearly observed at one and only one position in the sequence: the 5'-A residue Of $O_R1$. A band at A1 was virtually absent from the bound lanes at all protein concentrations, thus indicating that binding by 434 repressor was strongly and adversely affected by the analog at this site. Conversely, the relative intensity of the A1 band in the unbound lanes increased as the protein concentration was increased, again suggesting that DNA molecules having the analog at position −1 bind 434 repressor poorly.

Those skilled in the art will readily appreciate that all parameters listed herein are meant to be exemplary and actual parameters will depend upon the specific application for which the methods and apparatus of the present invention are being used. It is, therefore, to be understood that the foregoing embodiments are presented by way of example only and that, within the scope of the appended claims and equivalents thereto, the invention may be practiced otherwise than as specifically described:

What is claimed is:

1. A species of a formula:

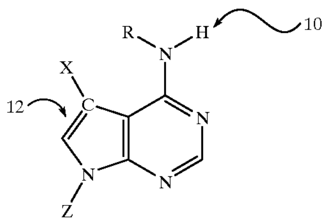

where X is a moiety allowing cleavage of double bond 12 under conditions tolerable by a protein-DNA complex, R is H or a hydrocarbon, and Z is an oligonucleotide, 2'-deoxyribose-5'triphosphate, or a functionality attachable to an oligonucleotide.

2. A species which is an oligonucleotide including at least one nitrogen base having a formula:

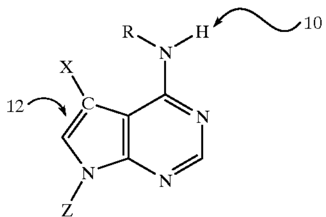

where X is a moiety allowing cleavage of double bond 12 under conditions tolerable by a protein-DNA complex, R is H or a hydrocarbon, and Z is the oligonucleotide.

3. A species as in either of claims 1 or 2, wherein R is H and X is selected so as not to be amenable to hydrogen bonding, and X and R are selected so as not to sterically interact in a way that would cause the species to twist appreciably and thereby to prevent the species from participating in normal Watson-Crick bonding.

4. A species as in either of claims 1 or 2, wherein R is H, and X is selected so as to hydrogen bond with R, and X and R are selected so as not to sterically interact in a way that would cause the species to twist appreciably and thereby to prevent the species from participating in normal Watson-Crick bonding.

5. A species as in either of claims 1 or 2, wherein R is a group not including a H amenable to hydrogen bonding.

6. A species as in any of claims 1–4, wherein R is H or a hydrocarbon group.

7. A species as in claim 6, wherein R is H or $CH_3$.

8. A species as in any preceeding claim, wherein X has electron-withdrawing capacity sufficient to render the double bond adjacent the carbon of the ring to which it is coupled clevable by aqueous base.

9. A species as in claim 8, wherein X is —CN, —Br, —Cl, —$NO_2$, —$SO_3^-$, —$SO_2R$, —COOH, or —F.

10. A species as in any of claims 1–8, wherein X is —$OCH_3$, —$CH_3$, —OH, an aromatic group, or —$NHCOCH_3$.

11. A species as in any preceeding claim, wherein R is H and X is —$NO_2$.

12. A species as in any preceeding claim, wherein Z is an oligonucleotide.

13. A method of determining contacts in a protein-DNA complex, comprising:

providing a plurality of end-labeled DNA strands each including, statistically, a nitrogen base of a formula:

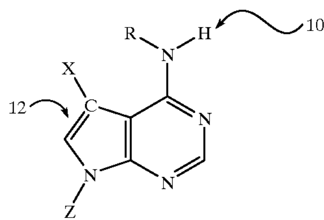

where X is a moiety allowing cleavage of double bond 12 under conditions tolerable by a protein-DNA complex, R is H or a hydrocarbon, and Z is an oligonucleotide, 2'-deoxyribose-5'triphosphate, or a functionality attachable to an oligonucleotide;

adding DNA-binding protein to the plurality of strands;

separating protein-bound from unbound DNA;

cleaving the DNA strands, and sequencing the DNA strands to determine a molecular weight region populated predominantly by the unbound strands and representative of cleavage sites indicating a protein binding site.

14. A method as in claim 13, further comprising determining contacts in a protein-DNA complex involving investigation with analogs of all four DNA bases, comprising:

providing a first group of DNA including a plurality of end-labeled DNA strands that each have, statistically, a TDI footprinting base analog of guanine;

providing a second group of DNA including a plurality of end-labeled DNA strands that each have, statistically, a TDI footprinting base analog of cytosine;

providing a third group of DNA including a plurality of end-labeled DNA strands that each have, statistically, a TDI footprinting base analog of thymine;

providing a fourth group of DNA including a plurality of end-labeled DNA strands that each have, statistically, a TDI footprinting base analog of adenine having the formula I;

adding DNA-binding protein to the plurality of strands of each group;

separating protein-bound from unbound DNA in each group;

cleaving the DNA strands of each group; and sequencing the DNA strands of each group to determine a molecular weight region populated predominantly by the unbound strands and representative of cleavage sites indicating a protein binding site.

15. A method as in either of claims 13 or 14, wherein R is H and X is selected so as not to be amenable to hydrogen bonding, and X and R are selected so as not to sterically interact in a way that would cause the species to twist appreciably and thereby to prevent the species from participating in normal Watson-Crick bonding.

16. A method as in either of claims 13 or 14, wherein R is H, and X is selected so as to hydrogen bond with R, and X and R are selected so as not to sterically interact in a way that would cause the species to twist appreciably and thereby to prevent the species from participating in normal Watson-Crick bonding.

17. A method as in either of claims 13 or 14, wherein R is a group not including a H amenable to hydrogen bonding.

18. A method as in any of claims 13–17, wherein R is H or a hydrocarbon group.

19. A method as in claim 18, wherein R is H or $CH_3$.

20. A method as in any of claims 13–19, wherein X has electron-withdrawing capacity sufficient to render its adjacent double bond clevable by aqueous base.

21. A method as in claim 20, wherein X is —CN, —Br, —Cl, —$NO_2$, —$SO_3^-$, —$SO_2R$, —COOH, or —F.

22. A method as in any of claim 13–19, wherein X is —$OCH_3$, —$CH_3$, —OH, an aromatic group, or —$NHCOCH_3$.

23. A method as in any of claim 13–22, wherein R is H and X is —$NO_2$.

24. A method as in any of claims 13–23, wherein Z is an oligonucleotide, 2'-deoxyribose-5'triphosphate, or a functionality attachable to an oligonucleotide.

* * * * *